United States Patent
Chen et al.

(10) Patent No.: US 12,339,202 B2
(45) Date of Patent: Jun. 24, 2025

(54) METHOD OF FAILURE ANALYSIS FOR DEFECT LOCATIONS

(71) Applicant: Shanghai Huali Integrated Circuit Corporation, Shanghai (CN)

(72) Inventors: Qiang Chen, Shanghai (CN); Jinde Gao, Shanghai (CN)

(73) Assignee: Shanghai Huali Integrated Circuit Corporation, Shanghai (CN)

(*) Notice: Subject to any disclaimer, the term of this patent is extended or adjusted under 35 U.S.C. 154(b) by 399 days.

(21) Appl. No.: 18/170,437

(22) Filed: Feb. 16, 2023

(65) Prior Publication Data

US 2023/0273101 A1 Aug. 31, 2023

(30) Foreign Application Priority Data

Feb. 28, 2022 (CN) .......................... 202210185334.5

(51) Int. Cl.
| | |
|---|---|
| *G01N 1/36* | (2006.01) |
| *G01N 23/04* | (2018.01) |
| *H01J 37/31* | (2006.01) |
| *H01J 37/317* | (2006.01) |

(52) U.S. Cl.
CPC .............. *G01N 1/36* (2013.01); *G01N 23/04* (2013.01); *H01J 37/3178* (2013.01); *G01N 2001/366* (2013.01); *G01N 2223/6116* (2013.01); *H01J 2237/31749* (2013.01)

(58) Field of Classification Search
CPC .... G01N 1/36; G01N 23/04; G01N 2001/366; G01N 2223/6116; H01J 37/3178; H01J 2237/31749
See application file for complete search history.

(56) References Cited

U.S. PATENT DOCUMENTS

| | | | | |
|---|---|---|---|---|
| 2002/0186028 A1* | 12/2002 | Xia | ..................... | G01R 31/307 |
| | | | | 324/754.22 |
| 2003/0206292 A1* | 11/2003 | Some | .................. | G01N 21/636 |
| | | | | 356/237.1 |
| 2014/0306381 A1* | 10/2014 | Raj | ................... | C04B 35/63416 |
| | | | | 264/434 |
| 2019/0048202 A1* | 2/2019 | Frauenrath | ............... | C09D 4/00 |
| 2022/0306476 A1* | 9/2022 | Cao | .................. | H01L 21/02601 |

* cited by examiner

*Primary Examiner* — Nicole M Ippolito
(74) *Attorney, Agent, or Firm* — Banner & Witcoff, Ltd.

(57) ABSTRACT

A method of failure analysis for locating open circuit defect in a metal layers, comprising: providing a chip sample having a metal layer, with an open circuit defect; delaminating the chip to expose the metal layer; depositing a metal conductive layer on the metal layer; removing a portion of the metal conductive layer to expose the metal layer; depositing a non-conductive protective layer to cover the exposed metal layer and any remaining portions of the metal conductive layer; preparing a TEM slice sample which comprises the metal layer, the remaining portions of the metal conductive layer, and the non-conductive protective layer; performing a VC analysis on the TEM slice sample to determine the defect position of the open circuit defect; and analyzing the defect position of the open circuit defect.

8 Claims, 4 Drawing Sheets

METHOD OF FAILURE ANALYSIS FOR DEFECT LOCATIONS

CROSS-REFERENCES TO RELATED APPLICATIONS

This application claims priority to Chinese patent application No. CN 202210185334.5, filed on Feb. 28, 2022 at CNIPA, and entitled "METHOD OF FAILURE ANALYSIS FOR DEFECT LOCATIONS", the disclosure of which is incorporated herein by reference in entirety.

TECHNICAL FIELD

The present application relates to the technical filed of semiconductors, in particular, to a failure analysis of structure positioning method.

BACKGROUND

In the integrated circuit process, failure of metal interconnection errors with increase metal layers has become an important failure source that affects the chip yield.

In the conventional method for analyzing an open circuit failure of metal interconnection, after a metal layer to be analyzed is exposed, one end of a metal wire is grounded using a laser or an ion beam while the other end is left floating. An open circuit position can be determined using a voltage contrast (VC) analysis method, and then a Transmission Electron Microscopy (TEM) slice analysis is performed at that position, in order to finally determine the root cause of the open circuit in the fabrication process.

With continuous advancing of the manufacturing process, defects that may cause the failures have become increasingly smaller in dimensions. Thus it is more challenging to find such tiny defects by applying the conventional failure analysis method, it is urgent to develop an improved defect locating analytical method to effectively locate the metal layer defects.

BRIEF SUMMARY

The present application provides a failure positioning method, to resolve the difficulties in determining the root cause of tiny defects in open circuits.

The present application provides a failure positioning method, at least including the following steps:
- step 1, providing a chip sample having a back end failure structure;
- step 2, delaminating the chip sample to expose a metal layer to be analyzed;
- step 3, depositing a metal conductive layer covering the metal layer on the surface of the chip sample;
- step 4, removing a portion of the metal conductive layer covering the metal layer on the surface of the chip sample to expose the metal layer;
- step 5, depositing a non-conductive protective layer covering the exposed metal layer and the remaining metal conductive layer on the surface of the chip sample;
- step 6, preparing a TEM slice sample containing the metal layer, the metal conductive layer, and the non-conductive protective layer from the chip sample;
- step 7, performing VC analysis on the TEM slice sample to determine an open circuit position; and
- step 8, analyzing the open circuit position on the TEM slice sample.

In an example, the metal conductive layer is deposited by means of a focused ion beam (FIB) in step 3.

In an example, the portion of the metal conductive layer covering the metal layer is removed by means of a FIB in step 4.

In an example, the non-conductive protective layer is deposited by means of a FIB in step 5.

In an example, the non-conductive protective layer in step 5 is a carbon protective layer.

In an example, the TEM slice sample is prepared by means of a FIB in step 6.

In an example, the VC analysis is performed on the TEM slice sample by means of a FIB in step 7.

In an example, the open circuit position on the TEM slice sample is analyzed by means of a TEM in step 8.

As described above, the failure positioning method of the present application has the following beneficial effects: the present application solves the difficulty in positioning a metal back end open circuit problem caused by tiny defects, and can directly perform the TEM analysis without reprocessing of the sample after the failure positioning, significantly improving the success rate and quality of the analysis.

DETAILED DESCRIPTION OF THE DISCLOSURE

The implementation manners of the present disclosure are described below using specific examples, and those skilled in the art could easily understand other advantages and effects of the present disclosure from the content disclosed in the Description. The present disclosure can also be implemented or applied in other different specific implementation manners, and various details in the Description can also be modified or changed based on different views and applications without departing from the spirit of the present disclosure.

Please refer to FIGS. 1-9. It should be noted that the figures provided in the embodiments are only intended to illustrate the basic concept of the present disclosure in a schematic way, so the figures only show the components related to the present disclosure instead of being drawn according to the number, shape, and size of components in actual implementation. The type, number, and proportion of the components in actual implementation can be changed randomly, and the layout type of the components may be more complex.

Figure 9:
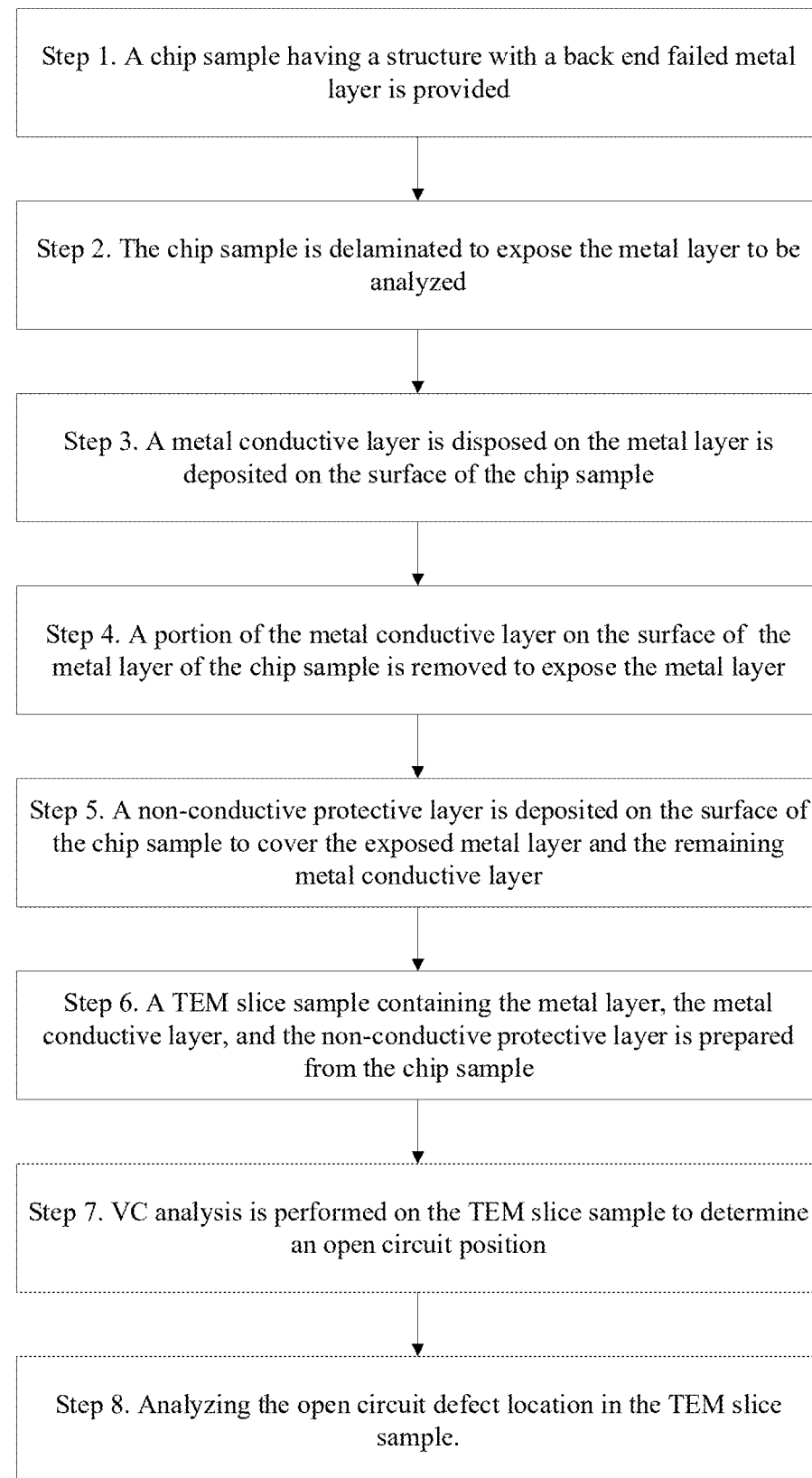
FIG. 9 is a flowchart of the failure analysis method for identifying metal defect positions according to the present disclosure.

The present disclosure provides a failure analysis of defect position method. Referring to FIG. 9, FIG. 9 is a flowchart of the failure analysis of metal defect position method in the present disclosure. The method at least includes the following steps.

Figure 1:
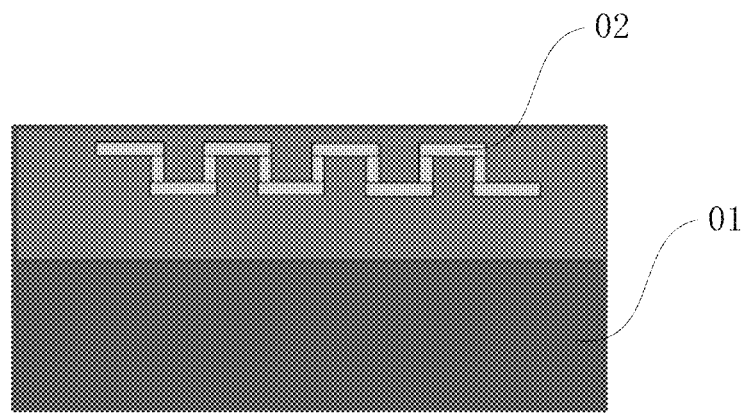
FIG. 1 is a schematic diagram of a longitudinal cross section of a chip sample structure according to the present disclosure.

Step 1. A chip sample having a structure with a back end failed metal layer is provided. Referring to FIG. 1, FIG. 1 is a schematic diagram of a longitudinal cross section of a chip sample structure according to the present disclosure. In step 1, the chip sample 01 having a back end structure failure is provided, and the back end failure structure in the chip sample is a metal layer 02.

Figure 2:
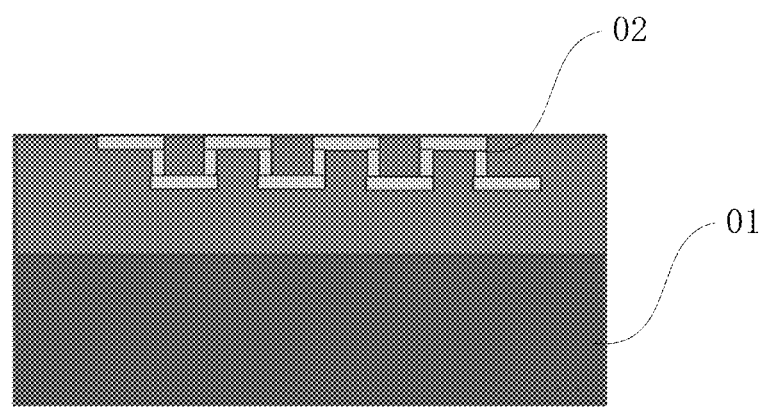
FIG. 2 is a schematic diagram of a longitudinal cross section structure in which a metal layer is exposed from top surface after delamination of the chip sample according to the present disclosure.

Step 2. The chip sample is delaminated to expose the metal layer to be analyzed. Referring to FIG. 2, FIG. 2 is a schematic diagram of a longitudinal cross section structure in which a metal layer is exposed from top surface after delamination of the chip sample according to the present disclosure. In step 2, the chip sample 01 is delaminated, that is, a sample layer covering the upper surface of the metal layer is removed, so as to expose the surface of the metal layer 02 to be analyzed.

Figure 3:
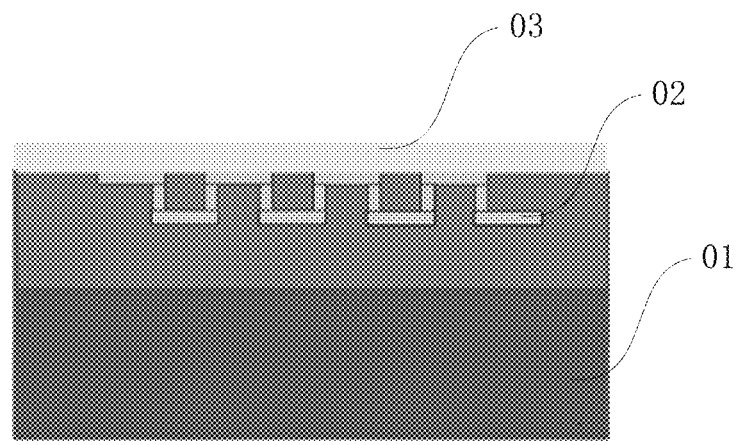
FIG. 3 is a schematic diagram of a longitudinal cross section structure in which a metal conductive layer covers the surface of the chip according to the present disclosure.

Step 3. A metal conductive layer is disposed on the metal layer is deposited on the surface of the chip sample. Referring to FIG. 3, FIG. 3 is a schematic diagram of a longitudinal cross section structure in which the metal conductive layer covers the surface of the chip sample in the present disclosure. In step 3, the metal conductive layer 03 covering the metal layer 02 is deposited on the surface of the chip sample. The metal conductive layer 03 is disposed on the metal layer 02, and a portion of the metal conductive layer is on top of the surface of the chip sample 01.

In this embodiment of the present disclosure, in step 3, the metal conductive layer 03 may be deposited by means of a FIB.

Figure 4:
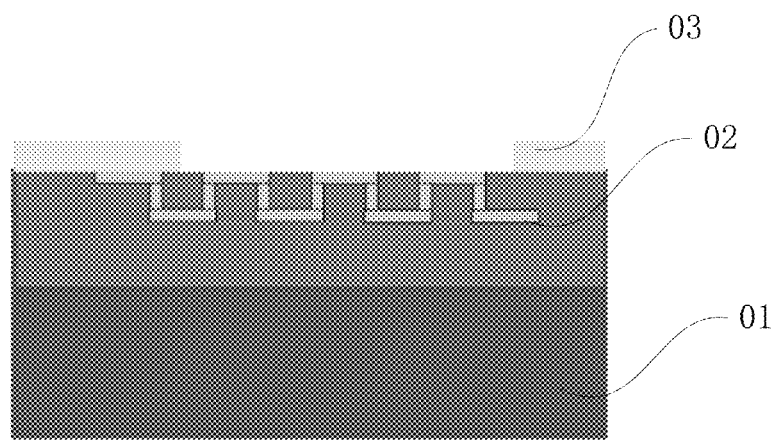
FIG. 4 is a schematic diagram of a longitudinal cross section structure of the chip sample in which the metal conductive layer is removed from the exposed metal layer according to the present disclosure.

Step 4. A portion of the metal conductive layer on the surface of the metal layer of the chip sample is removed to expose the metal layer. Referring to FIG. 4, FIG. 4 is a schematic diagram of a longitudinal section structure of the chip sample in which the metal conductive layer on the metal layer is removed in the present disclosure. In step 4, the portion of the metal conductive layer 03 on the surface of the metal layer 02 of the chip sample 01 is removed to expose the metal layer 02.

In this embodiment of the present disclosure, the portion of the metal conductive layer on the metal layer is removed by a FIB in step 4. In the present disclosure, the FIB refers to as a focused ion beam.

Figure 5:
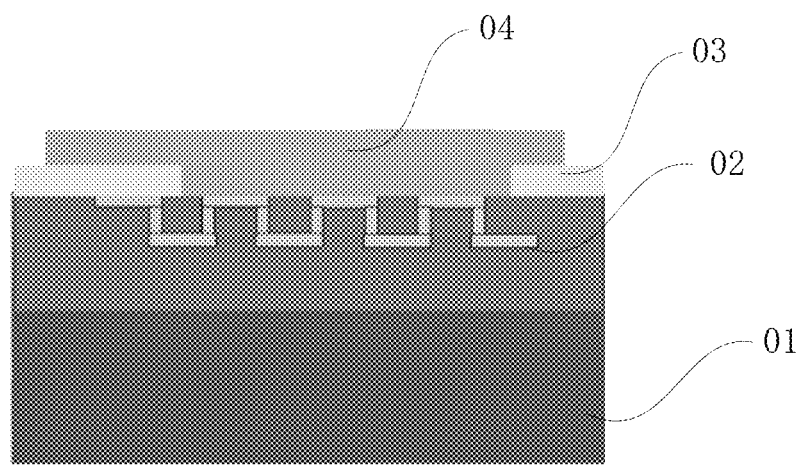
FIG. 5 is a schematic diagram of a longitudinal cross section structure of the chip sample in which a non-conductive protective layer is disposed on the metal layer according to the present disclosure.

Step 5. A non-conductive protective layer is deposited on the surface of the chip sample to cover the exposed metal layer and the remaining metal conductive layer. Referring to FIG. 5, FIG. 5 is a schematic diagram of a longitudinal cross section structure of the chip sample in which the non-conductive protective layer is disposed on the metal layer in the present disclosure. In step 5, the non-conductive protective layer 04 on the exposed metal layer 02 and the remaining metal conductive layer 03 is deposited on the surface of the chip sample 01.

In this embodiment of the present disclosure, the non-conductive protective layer 04 is deposited by means of a FIB in step 5.

In this embodiment of the present disclosure, the non-conductive protective layer 04 in step 5 may be a carbon protective layer.

Figure 6:
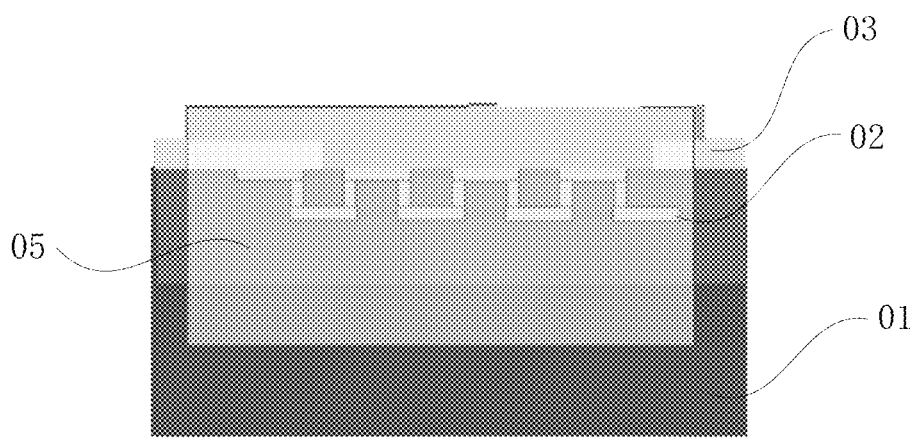
FIG. 6 is a schematic diagram of a structure in which a TEM slice sample is prepared from the chip sample according to the present disclosure.

Step 6. A TEM slice sample containing the metal layer, the metal conductive layer, and the non-conductive protective layer is prepared from the chip sample. Referring to FIG. 6, FIG. 6 is a schematic diagram of a structure in which the TEM slice sample is prepared from the chip sample in the present disclosure. In step 6, the TEM slice sample 05 containing the metal layer 02, the metal conductive layer 03, and the non-conductive protective layer 04 is prepared from the chip sample.

In this embodiment of the present disclosure, the TEM slice sample is prepared by means of a FIB in step 6.

Figure 7:
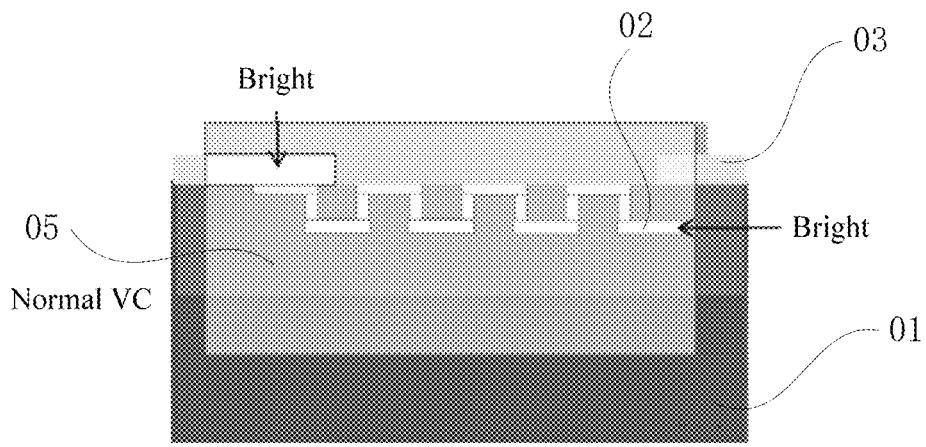
FIG. 7 is a schematic diagram of a structure of a normal VC in VC analysis performed on the TEM slice sample according to the present disclosure.
Figure 8:
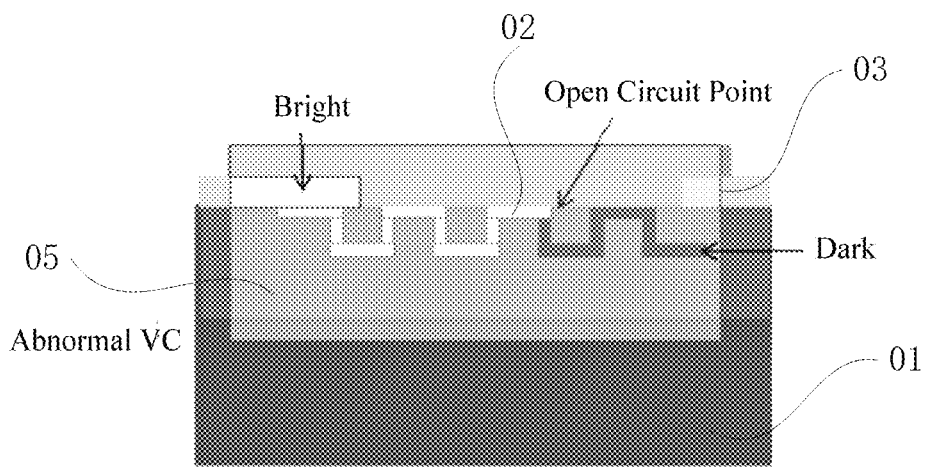
FIG. 8 is a schematic diagram of a structure of an abnormal VC (voltage contrast) in the VC analysis performed on the TEM slice sample, according to the present disclosure.

Step 7. VC analysis is performed on the TEM slice sample to determine an open circuit position. Referring to FIG. 7, FIG. 7 is a schematic diagram of a structure of a normal VC in the VC analysis performed on the TEM slice sample in the present disclosure. The VC in the present disclosure refers to a voltage contrast analysis method. FIG. 7 illustrates a case where no open circuit occurs in the TEM slice sample after the VC analysis. Both ends of the metal layer present a bright state during the test. Referring to FIG. 8, FIG. 8 is a schematic diagram of a structure of an abnormal VC in the VC analysis performed on the TEM slice sample in the present disclosure. FIG. 8 illustrates a case where an open circuit occurs in the TEM slice sample after the VC analysis. One of the two ends of the metal layer presents a bright state, and the other end presents a dark state.

In this embodiment of the present disclosure, the VC analysis is performed on the TEM slice sample by means of a FIB in step 7.

Step 8. Analyzing the open circuit defect location in the TEM slice sample.

In this embodiment of the present disclosure, the open circuit defect position in the TEM slice sample may be analyzed by means of a TEM in step 8.

To sum up, the disclosed method effectively locates those 1 open circuit tiny defects from the back end metal layers. The method enables performing a TEM analysis directly after the failure analysis of defect positions, without additional steps of reprocessing the sample after locating the defect position from the failure analysis, significantly reducing analysis time, improving the success rate and quality of the analysis. Therefore, the present method effectively overcomes various difficulties in the conventional technique, so it contributes significant utilization value in the industry.

The above embodiments merely exemplify the principle and effects of the present disclosure, and are not intended to limit the disclosure. Any person familiar with the art can modify or change the above embodiments without violating the spirit and scope of the disclosure. Therefore, all equivalent modifications or changes made by those with ordinary knowledge in the art without departing from the spirit and technical ideas disclosed by the present method shall still be covered by the claims of the present application.

What is claimed is:

1. A failure analysis method for locating a defect position, comprising following steps:

step 1, providing a chip sample having a metal layer, wherein the metal layer has an open circuit defect;

step 2, delaminating the chip sample to expose a top surface of the metal layer having the open circuit defect;

step 3, depositing a metal conductive layer on the metal layer of the chip sample;

step 4, removing a portion of the metal conductive layer from a top surface the metal layer to expose the metal layer;

step 5, depositing a non-conductive protective layer to cover the exposed metal layer and any remaining portions of the metal conductive layer of the chip sample;

step 6, preparing a TEM (Transmission Electron Microscopy) slice sample from the chip sample, wherein the TEM slice sample comprises the metal layer, the remaining portions of the metal conductive layer, and the non-conductive protective layer;

step 7, performing a VC (voltage contrast) analysis on the TEM slice sample to determine the defect position of the open circuit defect; and step 8, analyzing the defect position of the open circuit defect on the TEM slice sample.

2. The failure analysis method for locating the defect position according to claim 1, wherein the metal conductive layer is deposited by means of a FIB (focused ion beam) in step 3.

3. The failure analysis method for locating the defect position according to claim 1, wherein the portion of the metal conductive layer on the metal layer is removed by means of a FIB in step 4.

4. The failure analysis method for locating the defect position according to claim 1, wherein the non-conductive protective layer is deposited by means of a FIB in step 5.

5. The failure analysis method for locating the defect position according to claim 4, wherein the non-conductive protective layer in step 5 is a carbon protective layer.

6. The failure analysis method for locating the defect position according to claim 1, wherein the TEM slice sample is prepared by means of a FIB in step 6.

7. The failure analysis method for locating the defect position according to claim 1, wherein the VC analysis is performed on the TEM slice sample by means of a FIB in step 7.

8. The failure analysis method for locating the defect position according to claim 1, wherein the defect position of the open circuit defect on the TEM slice sample is analyzed by means of the TEM in step 8.

* * * * *